ns Patent [19]

Diel et al.

[11] Patent Number: 4,640,701
[45] Date of Patent: Feb. 3, 1987

[54] HERBICIDAL PHOSPHONIC ACID AND PHOSPHINIC ACID DERIVATIVES

[75] Inventors: Peter J. Diel, Riehen; Ludwig Maier, Arlesheim, both of Switzerland

[73] Assignee: Ciba-Geigy Corporation, Ardsley, N.Y.

[21] Appl. No.: 720,784

[22] Filed: Apr. 8, 1985

[30] Foreign Application Priority Data

Apr. 17, 1984 [CH] Switzerland .................. 1946/84

[51] Int. Cl.$^4$ .................. A01N 57/06; C07F 9/40; C07F 9/32
[52] U.S. Cl. .................. 71/86; 260/502.5 D; 558/179
[58] Field of Search .................. 260/951, 502.4 D; 71/86; 558/179

[56] References Cited

FOREIGN PATENT DOCUMENTS 0073040 2/1983 European Pat. Off. .
0078536 6/1983 European Pat. Off. .

OTHER PUBLICATIONS

J. General Chemistry 46, 1839(1946).

Primary Examiner—Anton H. Sutto
Attorney, Agent, or Firm—Edward McC. Roberts; Kevin T. Mansfield

[57] ABSTRACT

Novel phosphonic acid and phosphinic acid derivatives of the formula I

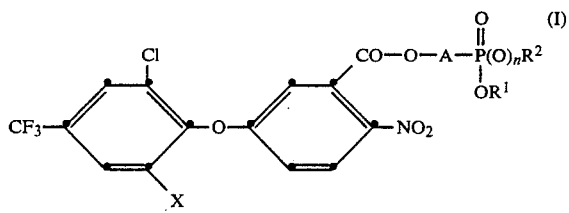

wherein
X is hydrogen or chlorine,
n is 0 or 1,
$R^1$ and $R^2$ are each independently hydrogen, $C_1$–$C_4$alkyl, $C_3$–$C_4$alkenyl, $C_3$–$C_4$alkynyl, $C_1$–$C_4$haloalkyl, $C_1$–$C_4$-alkoxy-$C_1$–$C_4$alkyl, $C_1$–$C_4$cyanoalkyl, or they are a phenyl radical, a phenyl-$C_1$–$C_4$alkyl radical or a naphthyl radical, each unsubstituted or substituted by halogen, $C_1$–$C_4$alkyl, $C_1$–$C_4$alkoxy, $C_1$–$C_4$haloalkyl, $C_1$–$C_4$haloalkoxy, nitro or cyano, and
A is a $C_1$–$C_3$alkyl chain which may be substituted by one or two $C_1$–$C_2$alkyl radicals and/or by one or two phenyl radicals, with the proviso that $R^2$ is not hydrogen if n is 0, have a good selective herbicidal activity. They are suitable for controlling monocot and dicot weeds pre- and postemergence in various crops of useful plants, e.g. cereals, maize, rice and soybeans.

18 Claims, No Drawings

HERBICIDAL PHOSPHONIC ACID AND PHOSPHINIC ACID DERIVATIVES

The present invention relates to novel herbicidal phosphonic acid and phosphinic acid derivatives, to the salts thereof, to the preparation thereof, to compositions containing them as active ingredients, and to the use thereof for selectively controlling weeds.

The novel phosphonic and phosphinic acid derivatives are of the formula I

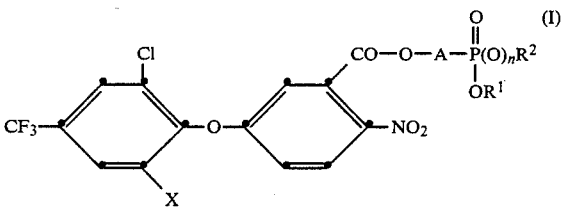

wherein
X is hydrogen or chlorine,
n is 0 or 1,
$R^1$ and $R^2$ are each independently hydrogen, $C_1$–$C_3$alkyl, $C_3$–$C_4$alkenyl, $C_3$–$C_4$alkynyl, $C_1$–$C_4$haloalkyl, $C_1$–$C_4$-alkoxy-$C_1$–$C_4$alkyl, $C_1$–$C_4$cyanoalkyl, or they are a phenyl radical, a phenyl-$C_1$–$C_4$alkyl radical or a naphthyl radical, each unsubstituted or substituted by one or two identical or different members from the group consisting of halogen, $C_1$–$C_4$alkyl, $C_1$–$C_4$alkoxy, $C_1$–$C_4$haloalkyl, $C_1$–$C_4$haloalkoxy, nitro and cyano, and
A is a $C_1$–$C_3$alkyl chain which may be substituted by one or two $C_1$–$C_2$alkyl radicals and/or by one or two phenyl radicals, with the proviso that $R^2$ is not hydrogen if n is 0.

In these definitions, halogen is fluorine, chlorine, bromine or iodine, with chlorine and bromine being preferred.

Alkyl radicals by themselves or as moiety of a combined alkyl ester may be straight chain or branched and contain the indicated number of carbon atoms. Representative examples of such alkyl radicals are methyl, ethyl, n-propyl, isopropyl, n-butyl, sec-butyl, tert-butyl and isobutyl.

$C_3$–$C_4$alkenyl or $C_3$–$C_4$alkynyl radicals $R^1$ and $R^2$ in the above definitions are likewise straight chain or branched radicals. Alkenyl radicals are in particular 2-propenyl (allyl), 2-methyl-2-propenyl (methallyl), 1-methyl-2-propenyl, 2-butenyl and 3-butenyl and alkynyl radicals are in particular 2-propynyl (propargyl), 2-butynyl and 3-butynyl. Preferred alkenyl radicals $R^1$ and $R^2$ are allyl, methallyl or 2-butenyl and preferred alkynyl radicals $R^1$ and $R^2$ are propargyl and 2-butynyl.

The phosphonic acid and phosphinic acid derivatives of formula I are novel and have good selective herbicidal properties. They are suitable for controlling monocot and, in particular, dicot weeds pre- and post-emergence in various crops of useful plants, e.g. cereals, maize, rice and soybeans.

Particularly advantageous phosphonic acid and phosphinic acid derivatives of formula I are those wherein X is hydrogen;
phosphonic acid derivatives of formula I, wherein X is hydrogen, n is 1, and A, $R^1$ and $R^2$ are as defined for formula I,
phosphinic acid derivatives of formula I, wherein X is hydrogen, n is 0, $R^1$ is as defined for formula I, and $R^2$ is $C_1$–$C_4$alkyl, or it is a phenyl radical or a naphthyl radical, each unsubstituted or substituted by one or two identical or different members selected from the group consisting of halogen, $C_1$–$C_4$alkyl, $C_1$–$C_4$alkoxy, $C_1$–$C_4$haloalkyl, $C_1$–$C_4$haloalkoxy, nitro and cyano.

Preferred individual compounds are:
O,O-diethylphosphonylmethyl 2-nitro-5-(2-chloro-4-trifluoromethylphenoxy)benzoate,
methyl-O-ethylphosphinylmethyl 2-nitro-5-(2-chloro-4-trifluoromethylphenoxybenzoate,
dihydroxyphosphonylmethyl 2-nitro-5-(2-chloro-4-trifluoromethylphenoxy)benzoate,
dihydroxyphosphonylmethyl 2-nitro-5-(2-chloro-4-trifluoromethylphenoxy)benzoate, isopropylamine salt,
O,O-diisopropylphosphonylmethyl 2-nitro-5-(2-chloro-4-trifluoromethylphenoxy)benzoate,
O,O-dimethylphosphonylmethyl 2-nitro-5-(2-chloro-4-trifluoromethylphenoxy)benzoate,
O,O-di-n-butylphosphonylmethyl 2-nitro-5-(2-chloro-4-trifluoromethylphenoxy)benzoate,
methyl-O-isopropylphosphinylmethyl 2-nitro-5-(2-chloro-4-trifluoromethylphenoxy)benzoate,
ethyl-O-ethylphosphinylmethyl 2-nitro-5-(2-chloro-4-trifluoromethylphenoxy)benzoate,
O,O-dimethylphosphonylethyl 2-nitro-5-(2-chloro-4-trifluoromethylphenoxy)benzoate,
dihydroxyphosphonylethyl 2-nitro-5-(2-chloro-4-trifluoromethylphenoxy)benzoate, isopropylamine salt,
O,O-dimethylphosphonylpropyl 2-nitro-5-(2-chloro-4-trifluoromethylphenoxy)benzoate and
dihydroxyphosphonylpropyl 2-nitro-5-(2-chloro-4-trifluoromethylphenoxy)benzoate, isopropylamine salt.

Herbicidal compounds with a similar chemical structure are known. 2-Nitro-5-(2-chloro-4-trifluoromethylphenoxy)benzoic acid is known from U.S. Pat. No. 3,928,416. Said benzoic acid has herbicidal properties but is fairly phytotoxic. Further, 2-nitro-5-(2-chloro-4-trifluoromethylphenoxy)benzoates with herbicidal properties are described in U.S. Pat. No. 3,941,830. European published application No. 73 040 describes phosphonylmethyl and phosphinylmethyl α-[4-(2,4-dichlorophenoxy)phenoxy]propionates, α-[4-(4-trifluoromethylphenoxy)phenoxy]propionates and α-[4-(5-trifluoromethylpyridyl-2-oxy)phenoxy]propionates with herbicidal properties. Finally, European published application No. 78 536 describes e.g. herbicidal 2-nitro-5-(2-chloro-4-trifluoromethylphenoxy)phenoxymethylphosphonic and 2-nitro-5-(2-chloro-4-trifluoromethylphenoxy)phenoxymethylphosphinic acids and esters. The activity of these compounds is often not satisfactory or only in some cases satisfactory.

The novel phosphonic acid and phosphinic acid derivatives of formula I according to claim 1 are prepared in a manner known per se by reacting 2-nitro-5-(2-chloro-4-trifluoromethylphenoxy)benzoic acid or the acid halide or a reactive ester thereof of formula II

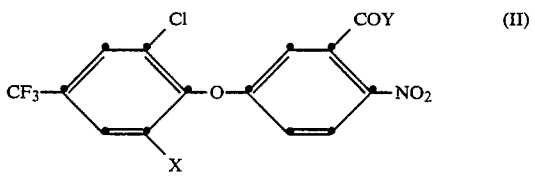

wherein
X is hydrogen or chlorine, and
Y is hydroxy, $C_1$–$C_4$alkoxy or halogen,
with a phosphinic acid or phosphonic acid derivative of formula III

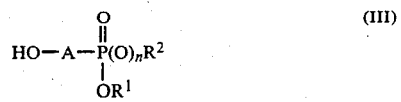

wherein A, n, $R^1$ and $R^2$ are as defined above, in an inert organic solvent and optionally in the presence of the equimolar amount of a base or a condensing agent, at a temperature in the range from −20° C. to the boiling point of the reaction mixture, and isolating the condensation product from the reaction mixture.

The reaction is advantageously carried out in an inert solvent. Suitable inert solvents are aromatic hydrocarbons such as benzene, toluene or xylene, and ethers such as diethyl ether, tetrahydrofuran and dioxane. The use of aromatic hydrocarbons is advisable, in particular when water of reaction forms which must be removed from the reaction mixture.

The reaction temperature may vary within wide limits. Suitable reaction temperatures are for example in the range from −20° C. to the reflux temperature of the reaction mixture. It is preferable to carry out the reaction at a temperature in the range from room temperature (20° C.) to 70° C.

It is advantageous to carry out the reaction of a compound of formula II, wherein Y is the hydroxyl group, either in the presence of anhydrous zinc chloride or strong sulfuric acid or in the presence of a catalytic amount of a strong acid such as sulfuric acid or p-toluenesulfonic acid, at reflux temperature in an aromatic hydrocarbon such as benzene, toluene or xylene as solvent, removing as an azeotrop the water formed. Further, it may be advantageous to carry out the reaction in the presence of a condensing agent such as N,N'-dicyclohexylcarbodiimide.

It is advantageous to carry out the reaction of a compound of formula II, wherein Y is a $C_1$–$C_4$alkoxy group, at reflux temperature in one of the above-mentioned solvents in the presence of a catalytic amount of a strong acid such as sulfuric acid or p-toluenesulfonic acid.

For the reaction of a compound of formula II, wherein Y is a halogen atom, the acid chlorides (Y=Cl) are particularly suitable. It is advantageous to carry out this reaction in the presence of at least the equivalent amount of a base as acid acceptor. Suitable bases are inorganic bases such as alkali metal carbonates and bicarbonates and alkaline earth metal carbonates and bicarbonates and organic bases such as tertiary amines, e.g. triethylamine, and pyridine. 2-Nitro-5-(2-chloro-4-trifluoromethylphenoxy)benzoic acid and its derivatives are known e.g. from U.S. Pat. Nos. 3,979,437, 3,928,416 and 3,784,635.

Said benzoic acid and its derivatives are prepared by reacting a 5-hydroxy-2-nitrobenzoic acid derivative with 1,2-dichloro-4-trifluoromethylbenzene in an inert organic solvent and in the presence of a base.

A large number of the starting compounds of formula III and the preparation thereof have already been described in the literature. Those compounds of formula III which have not yet been described can be prepared in analogous manner. Thus, compounds of formula III, wherein A is a methylene group which is unsubstituted or substituted by one or two $C_1$–$C_2$alkyl radicals or by one or two phenyl radicals, can be obtained in particularly suitable manner by reacting a phosphonate or a phosphonite with a suitable carbonyl compound in accordance with equation 2:

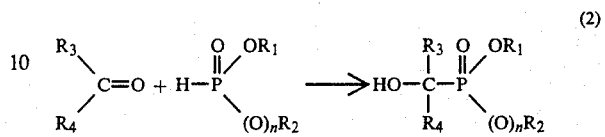

In equation 2, each of $R_3$ and $R_4$ independently of the other is hydrogen, $C_1$–$C_2$alkyl or phenyl, and $R_1$, $R_2$ and n are as defined for formula I.

Reactions of this type are described for example in "Organic Phosphorus Compounds" (John Wiley & Sons, New York) Vol. 6, page 26, and Vol. 7, page 30, and in J. Gen. Chem. 46, 1839 (1946).

Compounds of formula III, wherein A is a 1,2-ethylene or a 1,3-propylene group which is mono- or disubstituted by one substituent selected from the group $C_1$–$C_2$alkyl and phenyl, can be prepared in accordance with equation 3 by addition of a phosphonate or a phosphonite to a vinyl carboxylate or in accordance with equation 4 by addition of a phosphonate or a phosphonite to an allyl carboxylate and subsequently hydrolysing or alcoholising the 2-acyloxyethyl or 3-acyloxypropyl phosphonate or phosphinate initially obtained.

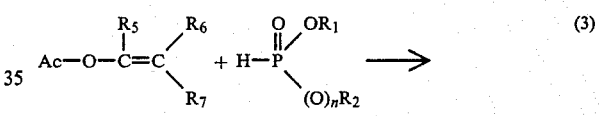

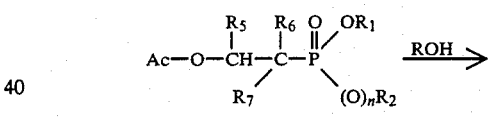

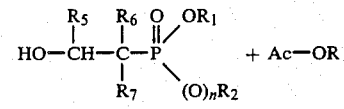

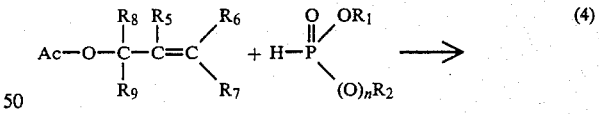

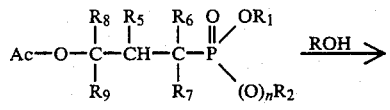

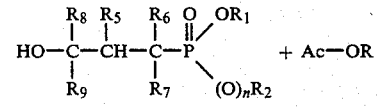

In each of equations 3 and 4, the radicals $R_5$, $R_6$, $R_7$, $R_8$ and $R_9$ are hydrogen, $C_1$–$C_2$alkyl or phenyl, but in each case not more than 2 of these radicals may have a meaning other than hydrogen. $R_1$, $R_2$ and n are as defined for formula I, Ac is the acyl radical of a carboxylic acid, preferably acetic acid, and R is hydrogen, sodium, potassium or $C_1$–$C_4$alkyl. Such reactions are described for example in "Organic Phosphorus Compounds" (John Wiley & Sons, New York) Vol. 6, page 34, and Vol. 7, page 28, and in J. Amer. Chem. Soc. 77, 6225 (1955) and ibid. 81, 6275 (1959).

Further, compounds of formula III, wherein A is a 1,2-ethylene or a 1,3-propylene group which is unsubstituted or mono- or disubstituted by $C_1$-$C_2$alkyl and phenyl, can be obtained in accordance with equation 5 by the Michaelis-Arbusov reaction of phosphites and phosphonites with corresponding 2-haloethyl or 3-halopropyl esters of carboxylic acids and subsequently hydrolysing or alcoholising the corresponding 2-acyloxyethyl or 3-acyloxypropyl phosphonates or phosphinates.

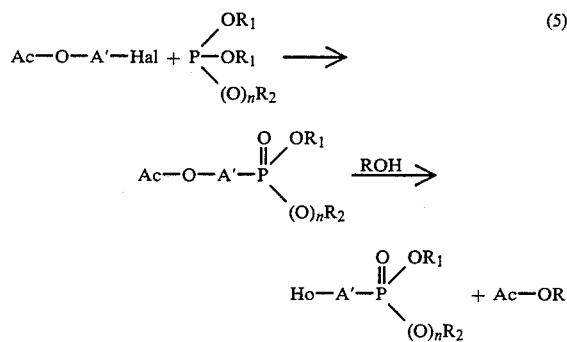

In equation 5, $R_1$, $R_2$ and n are as defined for formula I, A' is a 1,2-ethylene or a 1,3-propylene group which may be mono- or disubstituted by one substituent from the group $C_1$-$C_2$alkyl and phenyl, Ac is the acyl radical of a carboxylic acid, and R is hydrogen, sodium, potassium or $C_1$-$C_4$alkyl. Such reactions are described for example in "Organic Phosphorus Compounds" (John Wiley & Sons, New York) Vol. 6, page 14, and Vol. 7, page 23, and in J. Amer. Chem. Soc. 78. 6025 (1956). Further, in this connection attention is drawn to German Offenlegungsschrift 2 313 255.

The present invention also comprises the preparation of agrochemical compositions.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils, epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstitued or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp., Ridgewood, New Jersey, 1981; H. Stache, "Tensid-Taschenbuch", 2nd Edition, C. Hanser Verlag, Munich & Vienna, 1981; M. and J. Ash, "Encyclopedia of Surfactants", Vol. I-III, Chemical Publishing Co., New York, 1980–81.

The agrochemical compositions usually contain 0.1 to 99%, preferably 0.1 to 95%, of a compound of formula I, 1 to 99.9% of a solid or liquid adjuvant, and 0 to 25%, preferably 0.1 to 25%, of a surfactant.

Preferred formulations are composed in particular of the following constituents (% =percentage by weight):

| Solutions | | |
|---|---|---|
| active ingredient | 5 to 95%, | preferably 10 to 80% |
| solvent | 95 to 5%, | preferably 90 to 0% |
| surfactant | 1 to 30%, | preferably 2 to 20% |
| Emulsifiable concentrates | | |
| active ingredient | 10 to 50%, | preferably 10 to 40% |
| surfactant | 5 to 30%, | preferably 10 to 20% |
| liquid carrier | 20 to 95%, | preferably 40 to 80% |
| Dusts | | |
| active ingredient | 0.5 to 10%, | preferably 2 to 8% |
| solid carrier | 99.5 to 90%, | preferably 98 to 92% |
| Suspension concentrates | | |
| active ingredient | 5 to 75%, | preferably 10 to 50% |
| water | 94 to 25%, | preferably 90 to 30% |
| surfactant | 1 to 40%, | preferably 2 to 30% |
| Wettable powders | | |
| active ingredient | 0.5 to 90%, | preferably 1 to 80% most preferably 20 to 60% |
| surfactant | 0.5 to 20%, | preferably 1 to 15% |
| solid carrier | 5 to 90%, | preferably 30 to 70% |
| Granulates | | |
| active ingredient | 0.5 to 30%, | preferably 3 to 15% |
| solid carrier | 99.5 to 70%, | preferably 97 to 85%. |

Whereas commercial products will be preferably formulated as concentrates, the end user will normally employ dilute formulations. The formulations can be diluted to a concentration as low as 0.001% of active ingredient.

The compositions may also contain further ingredients such as stabilisers, antifoams, viscosity regulators, binders, tackifiers, as well as fertilisers and other compounds for obtaining special effects.

Such agrochemical compositions constitute an object of the present invention.

The invention is illustrated in more detail by the following Examples. It is, however, not restricted to these Examples.

Example 1

Preparation of O,O-diethylphosphonylmethyl 2-nitro-5-(2-chloro-4-trifluoromethylphenoxy)benzoate

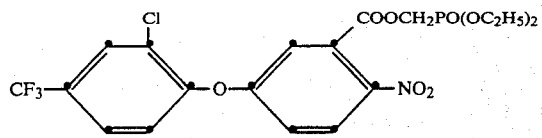

A reaction vessel is charged with 4.4 g (0.025 ml) of hydroxymethyl -O,O-diethyl phosphonate, 3.7 ml (0.026 mol) of triethylamine and 0.3 g of 4-piperidinopyridine in 100 ml of tetrahydrofuran. At room temperature and with stirring, a solution of 10 g (0.026 mol) of 2-nitro-5-(2-chloro-4-trifluoromethylphenoxy)benzoyl chloride in 50 ml of tetrahydrofuran is slowly added dropwise to the reaction mixture. The reaction is exothermic and triethylammonium hydrochloride is precipitated. The batch is stirred for 1 hour at 37° C. and for 1 hour at 70° C. and then allowed to cool. The salt is filtered with suction and the filtrate is concentrated by rotary evaporation and subsequently dried under high vacuum. The 16.2 g of residual oil are chromatographed over silica gel eluted with $CH_2CH_2$/MeOH 95:5.

Yield: 11.4 g (85% of theory) of oil $n_D^{20}$: 1.5236.

EXAMPLE 2

Preparation of methyl-O-ethylphosphinylmethyl 2-nitro-5-(2-chloro-4-trifluoromethylphenoxy)benzoate

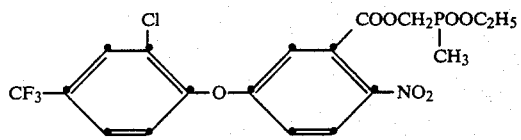

A reaction vessel is charged with 10 g (0.072 mol) of hydroxymethylmethyl-O-ethyl phosphinate, 10 ml (0.072 mol) of triethylamine and 0.5 g of 4-piperidinopyridine in 150 ml of toluene. With stirring, a solution of 27.5 g (0.072 mol) of 2-nitro-5-(2-chloro-4-trifluoromethylphenoxy)benzoyl chloride in 50 ml of toluene is added dropwise to the reaction mixture. The temperature rises to 50° C. and triethylamine hydrochloride is precipitated. The batch is stirred for 1 hour at 50° C. and for 1 hour at 70° C. The precipitate is filtered with suction and the filtrate is concentrated by rotary evaporation. The residual oil (37 g) is dried under high vacuum at 50° C. and then chromatographed over silica gel eluted with $CH_2Cl_2$/MeOH 95:5.

Yield: 26.1 g (75% of theory) $n_D^{20}$: 1.5350.

EXAMPLE 3

Preparation of dihydroxyphosphonylmethyl 2-nitro-5-(2-chloro-4-trifluoromethylphenoxy)benzoate

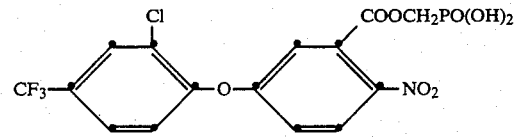

A reaction vessel is charged with 5 g (0.0093 mol) of O,O-diisopropylphosphonylmethyl 2-nitro-5-(2-chloro-4-trifluoromethylphenoxy)benzoate in 100 ml of chloroform. With stirring, 3.75 ml (0.0278 mol) of trimethylbromosilane are added dropwise at room temperature to the reaction mixture. The batch is stirred for 2 hours at 70° C. and then overnight at room temperature. The chloroform is subsequently removed by rotary evaporation and the residual oil is dried under high vacuum. The oil is stirred in ethanol and the yellow solution is concentrated again by rotary evaporation and subsequently dried at 0.2 mbar and 50° C. The free acid is converted in ethanol into the salt by adding 2.5 equivalents of isopropylamine.

Yield: 2.1 g, melting point = 105° C. decomp., (sinters at 96°-100° C.).

The following compounds are obtained in a manner analogous to those of these Examples:

TABLE 1

$$\text{CF}_3\text{-}\underset{X}{\underset{|}{\text{C}_6\text{H}_2}}\text{(Cl)-O-C}_6\text{H}_3(\text{NO}_2)\text{-CO-O-A-P(O)}_n\text{R}^2(\text{OR}^1) \quad (I)$$

| No. | A | R¹ | R² | n | X | Physical data |
|---|---|---|---|---|---|---|
| 1.01 | CH₂ | C₂H₅ | C₂H₅ | 1 | H | $n_D^{20}$ 1.5236 |
| 1.02 | CH₂ | C₂H₅ | CH₃ | 0 | H | $n_D^{20}$ 1.5350 |
| 1.03 | CH₂ | H | H | 1 | H | isopropylamine salt m.p. 105° decomp. |
| 1.04 | CH₂ | C₃H₇iso | C₃H₇iso | 1 | H | $n_D^{20}$ 1.5131 |
| 1.05 | CH₂ | CH₃ | CH₃ | 1 | H | $n_D^{20}$ 1.5315 |
| 1.06 | CH₂ | C₄H₉n | C₄H₉n | 1 | H | $n_D^{20}$ 1.5040 |
| 1.07 | CH₂ | C₃H₇iso | CH₃ | 0 | H | $n_D^{20}$ 1.5243 |
| 1.08 | CH₂ | C₂H₅ | C₂H₅ | 0 | H | analysis |
| calculated: | | | C 46.03% H 3.66% F 11.5% N 2.82% P 6.25% | | | |
| found: | | | C 45.2% H 3.6% F 11.1% N 2.8% P 6.3% | | | |
| 1.09 | CH₂ | H | CH₃ | 0 | H | isopropylamine salt m.p. 58° decomp. |
| 1.10 | CHCH₃ | CH₃ | CH₃ | 1 | H | m.p. 117-119° |
| 1.11 | CH(C₂H₅) | CH₃ | CH₃ | 1 | H | oil |
| 1.12 | CHCH₃ | C₂H₅ | CH₃ | 1 | H | oil |
| 1.13 | CHCH₃ | CH₃ | CH₃ | 1 | H | $n_D^{20}$ 1.5278 |
| 1.14 | CH₂CH₂ | CH₃ | CH₃ | 1 | H | $n_D^{20}$ 1.5320 |
| 1.15 | CH₂CH₂CH₂ | H | H | 1 | H | isopropylamine salt m.p. 40-50° |
| 1.16 | CH₂CH₂ | H | H | 1 | H | isopropylamine salt m.p. 48-53° |

Formulation Examples

EXAMPLE 4

Formulation Examples for liquid active ingredients of formula I (throughout, percentages are by weight)

| (a) Emulsifiable concentrates | (a) | (b) | (c) |
|---|---|---|---|
| a compound of Table 1 | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| (b) Solutions | (a) | (b) | (c) | (d) |
|---|---|---|---|---|
| a compound of Table 1 | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| petroleum distillate (boiling range 160-190°) | — | — | 94% | — |

These solutions are suitable for application in the form of microdrops.

| (c) Granulates | (a) | (b) |
|---|---|---|
| a compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | (a) | (b) |
|---|---|---|
| a compound of Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

EXAMPLE 5

Formulation examples for solid compounds of formula I (throughout, percentages are by weight)

| (a) Wettable powders | (a) | (b) |
|---|---|---|
| a compound of Table 1 | 20% | 60% |
| sodium lignosulfonate | 5% | 5% |
| sodium lauryl sulfate | 3% | — |
| sodium diisobutylnaphthalenesulfonate | — | 6% |
| octylphenol polyethylene glycol ether (7-8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | |
|---|---|
| a compound of Table 1 | 10% |
| octylphenol polyethylene glycol ether (4-5 moles of ethylene oxide) | 3% |
| calcium dodecylbenzenesulfonate | 3% |

-continued (b) Emulsifiable concentrate

| | |
|---|---|
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| (c) Dusts | (a) | (b) |
|---|---|---|
| a compound of Table 1 | 5% | 8% |
| talcum | 95% | — |
| kaolin | — | 92% |

Ready-for-use dusts are obtained by mixing the active ingredient with the carriers, and grinding the mixture in a suitable mill.

| (d) Extruder granulate | |
|---|---|
| a compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| (e) Coated granulate | |
|---|---|
| a compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | |
|---|---|
| a compound of Table 1 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

Biological Examples

The selective herbicidal activity was determined in a greenhouse by various plant tests. In these tests, the activity of compound 5 was compared with that of 0,0-diisopropylphosphonylmethyl 4-(5-tri-fluoromethylpyridyl-2-oxy)phenoxypropionate of the formula

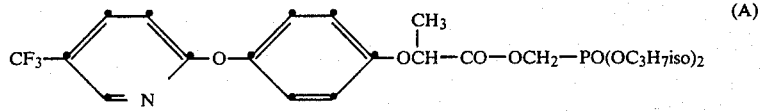

which is known from European published application No. 73 040.

EXAMPLE 6

Preemergence test

In a greenhouse, plant seeds are sown in flower pots of 11 cm diameter, so that per pot 12 to 30 plants can develop. Immediately after sowing, the surface of the soil is sprayed with an aqueous emulsion of the test compound obtained by diluting an emulsifiable concentrate with water. Various concentrations are applied and the amount of active ingredient is calculated in kg per hectare. The pots are then kept in the greenhouse at 22°–25° C. and 50–70% relative humidity and the plants are watered regularly. The test is evaluated 3 weeks later. The state of the plants is assessed in accordance with the following rating:
1: plant has not germinated or it has died
2–3: very severe damage
4: severe damage
5: moderate damage, stunted growth
6: damage, plant is able to regenerate
7–8: slight damage
9: normal growth, as untreated plants.
The results are shown in Table 2.

TABLE 2

| Compound Concentration in kg/ha | No. 5 | | | | A | | | |
|---|---|---|---|---|---|---|---|---|
| | 4 | 2 | 1 | ½ | 4 | 2 | 1 | ½ |
| Plant | | | | | | | | |
| wheat | 6 | 7 | 9 | 9 | 1 | 1 | 1 | 5 |
| maize | 4 | 4 | 8 | 9 | 1 | 1 | 1 | 1 |
| soybean | 7 | 8 | 9 | 9 | 9 | 9 | 9 | 9 |
| cotton | 6 | 8 | 9 | 9 | 9 | 9 | 9 | 9 |
| Echinochloa crus galli | 3 | 5 | 8 | 9 | 1 | 1 | 1 | 1 |
| Abutilon | 3 | 5 | 7 | 9 | 9 | 9 | 9 | 9 |
| Chenopodium sp | 1 | 1 | 1 | 5 | 9 | 9 | 9 | 9 |
| Sinapis alba | 1 | 1 | 1 | 7 | 8 | 8 | 9 | 9 |
| Galium aparine | 2 | 3 | 8 | 9 | 9 | 9 | 9 | 9 |
| Viola tricolor | 1 | 1 | 1 | 4 | 9 | 9 | 9 | 9 |
| Beta vulgaris | 1 | 1 | 1 | 4 | 9 | 9 | 9 | 9 |

EXAMPLE 7

Postemergence test

Various cultivated plants and weeds are grown from seeds in pots in a greenhouse until they have attained the 4- to 6-leaf stage. The plants are then sprayed with an aqueous emulsion of test compound corresponding to a concentration of 125 to 1000 g per hectare. The plants are then kept at optimum conditions of light, temperature (22°–25° C.) and humidity (50–70% relative) and regular watering. The test is evaluated 15 days after treatment in accordance with the same rating as for the preemergence test. The results are shown in Table 3:

TABLE 3

| Compound Concentration g/ha | No. 5 | | | | A | | | |
|---|---|---|---|---|---|---|---|---|
| | 1000 | 500 | 250 | 125 | 1000 | 5000 | 250 | 125 |
| Plant | | | | | | | | |
| wheat | 7 | 8 | 8 | 9 | 3 | 4 | 4 | 7 |
| maize | 4 | 5 | 7 | 8 | 1 | 2 | 4 | 4 |
| soybean | 6 | 7 | 7 | 7 | 9 | 9 | 9 | 9 |
| Echinochloa crus galli | 2 | 2 | 4 | 5 | 1 | 1 | 3 | 4 |
| Cyperus esc. | 2 | 2 | 4 | 5 | 9 | 9 | 9 | 9 |
| Abutilon sp. | 1 | 1 | 3 | 4 | 9 | 9 | 9 | 9 |
| Xanthium sp. | 1 | 1 | 2 | 3 | 9 | 9 | 9 | 9 |
| Chenopodium sp | 2 | 2 | 2 | 3 | 9 | 9 | 9 | 9 |
| Ipomoea purp. | 1 | 1 | 1 | 2 | 9 | 9 | 9 | 9 |
| Sinapis alba | 1 | 1 | 1 | 1 | 7 | 8 | 9 | 9 |
| Galium aparine | 1 | 1 | 2 | 2 | 8 | 8 | 9 | 9 |
| Viola tricolor | 1 | 1 | 1 | 1 | 8 | 9 | 9 | 9 |
| Beta vulgaris | 1 | 2 | 3 | 4 | 7 | 8 | 8 | 9 |

EXAMPLE 8

Test on rice

In a further test the postemergence activity of these compounds is tested using young rice plants which grow in water, together with related weeds.

Twenty-five-day-old rice plants are transplanted into large rectangular asbestos cement containers in a greenhouse. Seeds of the weeds occuring in rice crops, namely Echinochloa, Scirpus, Monocharia and Sagittaria, are then sown between the rows of rice plants. The containers are well watered and kept at a temperature of about 25° C. and at high humidity. Twelve days later, when the weeds have emerged and reached the 2-3 leaf stage, the soil in each of the containers is covered with a layer of water to a height of 2.5 cm. The test compound is then applied in the form of an emulsifiable concentrate with a pipette between the rows of plants. The emulsifiable concentrate is diluted and applied such that it corresponds to a field application rate of 2, 1, ½ and ¼ kg/ha respectively. The test is evaluated 4 weeks later and the state of the plants is assessed in accordance with the same rating as for the preemergence test. The results are shown in Table 4:

TABLE 4

| Compound Concentration kg/ha | No. 5 | | | | A | | | |
|---|---|---|---|---|---|---|---|---|
| | 2 | 1 | ½ | ¼ | 2 | 1 | ½ | ¼ |
| rice | 5 | 6 | 6 | 7 | 2 | 2 | 5 | 8 |
| Echinochloa crus galli | 1 | 1 | 3 | 3 | 1 | 1 | 1 | 1 |
| Scirpus | 3 | 4 | 5 | 7 | 5 | 8 | 9 | 9 |
| Monocharia vag. | 3 | 3 | 4 | 4 | 6 | 9 | 9 | 9 |
| Sagittaria pyg. | 8 | 9 | 9 | 9 | 9 | 9 | 9 | 9 |

The activity of compound A is specifically tested on monocot plants.

What is claimed is:

1. A phosphonic acid or phosphinic acid derivative of the formula

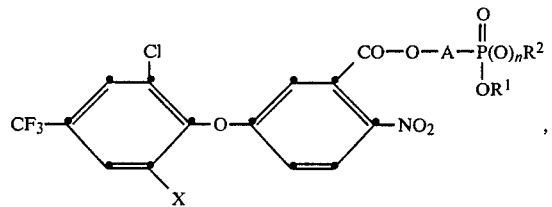

wherein
X is hydrogen,
n is 0 or 1,
$R^1$ and $R^2$ are each independently hydrogen or $C_1$-$C_4$alkyl and
A is a $C_1$-$C_3$alkyl chain which may be substituted by one or two $C_1$-$C_2$alkyl radicals, with the proviso that $R^2$ is not hydrogen if n is 0.

2. A herbicidal composition which contains, as active ingredient, a phosphonic acid or phosphinic acid derivative of formula I according to claim 1, together with inert adjuvants.

3. A phosphonic acid derivative according to claim 1, wherein n is 1, $R^1$ is as defined in claim 1 and $R^2$ is hydrogen or $C_1$-$C_3$alkyl.

4. A phosphinic acid derivative according to claim 1, wherein n is 0, $R^2$ is $C_1$-$C_2$alkyl, and $R^1$ is as defined in claim 1.

5. O,O-Diethylphosphonylmethyl 2-nitro-5-(2-chloro-4-trifluoromethylphenoxy)benzoate according to claim 1.

6. Methyl-O-ethylphosphinylmethyl 2-nitro-5-(2-chloro-4-trifluoro-methylphenoxy)benzoate according to claim 1.

7. Dihydroxyphosphonylmethyl 2-nitro-5-(2-chloro-4-trifluoromethylphenoxy)benzoate according to claim 1.

8. Dihydroxyphosphonylmethyl 2-nitro-5-(2-chloro-4-trifluoromethylphenoxy)benzoate, isopropylamine salt, according to claim 1.

9. O,O-Diisopropylphosphonylmethyl 2-nitro-5-(2-chloro-4-trifluoromethylphenoxy)benzoate according to claim 1.

10. O,O-Dimethylphosphonylmethyl 2-nitro-5-(2-chloro-4-trifluoromethylphenoxy)benzoate according to claim 1.

11. O,O-Di-n-butylphosphonylmethyl 2-nitro-5-(2-chloro-4-trifluoromethylphenoxy)benzoate according to claim 1.

12. Methyl-O-isopropylphosphinylmethyl 2-nitro-5-(2-chloro-4-trifluoromethylphenoxy)benzoate according to claim 1.

13. Ethyl-O-ethylphosphinylmethyl 2-nitro-5-(2-chloro-4-trifluoromethylphenoxy)benzoate according to claim 1.

14. O,O-Dimethylphosphonylethyl 2-nitro-5-(2-chloro-4-trifluoromethylphenoxy)benzoate according to claim 1.

15. Dihydroxyphosphonylethyl 2-nitro-5-(2-chloro-4-trifluoromethylphenoxy)benzoate, isopropylamine salt, according to claim 1.

16. O,O-Dimethylphosphonylpropyl 2-nitro-5-(2-chloro-4-trifluoromethylphenoxy)benzoate according to claim 1.

17. A method of selectively controlling weeds in crops of useful plants, which method comprises applying to said plants or to the locus thereof a herbicidally effective amount of a phosphonic acid or phosphinic acid derivative of formula I according to claim 1.

18. A method of selectively controlling weeds in crops of cereals, maize, rice and soybeans, which method comprises applying to said crops or to the locus thereof a herbicidally effective amount of a phosphonic acid or phosphinic acid derivative of formula I according to claim 1.

* * * * *